(12) United States Patent
Wagner

(10) Patent No.: US 6,902,719 B2
(45) Date of Patent: Jun. 7, 2005

(54) REVERSE ISOTOPE DILUTION ASSAY AND LACTOSE INTOLERANCE ASSAY

(76) Inventor: David A. Wagner, 460 Amherst St., Nashua, NH (US) 03063

(*) Notice: Subject to any disclaimer, the term of this patent is extended or adjusted under 35 U.S.C. 154(b) by 0 days.

(21) Appl. No.: 10/094,309

(22) Filed: Mar. 7, 2002

(65) Prior Publication Data

US 2002/0159950 A1 Oct. 31, 2002

Related U.S. Application Data

(63) Continuation of application No. PCT/US01/15143, filed on May 10, 2001.
(60) Provisional application No. 60/205,342, filed on May 18, 2000.

(30) Foreign Application Priority Data

Jan. 18, 2002 (JP) .................................. 2001-583819

(51) Int. Cl.[7] .................. A61K 51/00; A61M 36/14
(52) U.S. Cl. ................ 424/1.81; 424/1.11; 424/1.65; 424/9.1; 424/9.2; 424/1.73
(58) Field of Search ............... 424/1.11, 1.65, 424/1.69, 9.1, 1.81, 9.2, 94.1; 435/183, 173

(56) References Cited

U.S. PATENT DOCUMENTS 6,186,958 B1 2/2001 Katzman

OTHER PUBLICATIONS

Harrison, M. and Walker–Smith, J.A., Gut, Jan. 1977, p. 48–52, v. 18–1, BMJ Publishing Group, UK.
Davidson, G.P., et al., J. Pediatr., Oct. 1984, p. 587–90, v. 105–4, Elsevier Science, USA.
Douwes, A. C., et al., Arch. Dis. Child. Apr. 1985, p. 333–7, v. 60–4, BMJ Publishing Group, UK.
Arola, H. Scand. J. Gastroenterol., Apr. 1994, p. 26–35, v. 29–Suppl 202, Taylor and Francis Ltd., Norway.
Suarez, F.L., et al., N. Engl. J. Med., Jul. 1995, p. 1–4, v. 333–1, The Massachusetts Medical Society, USA.
Stallings, V.A., Am J. Ther. Jul. 1997, p. 259–273, v. 4–7/8, Chapman & Hall, UK.
Carrocio, A., et al., J. Am. Coll. Nutr., Dec. 1998, p. 631–36, v. 17–6, Am. Coll. Nutr., USA.
Saltzman, J.R., et al., Am. J. Clin. Nutr., Jan. 1999, p. 140–6, v. 69–1, Am. Soc. Clin. Nutr., USA.
Peuhkuri, K., et al., Am. J. Clin. Nutr., Feb. 2000, p. 600–1, v. 71–2, Am. Soc. Clin. Nutr., USA.

*Primary Examiner*—Dameron L. Jones

(57) ABSTRACT

A "reverse isotope dilution assay" herein, wherein a pathway that produces a given metabolite is assayed by diluting a labelled metabolite produced by a second constitutive pathway. In one aspect, the invention relates to a method for monitoring lactose maldigestion or lactose intolerance in humans. Specifically, the method requires administering a reverse tracer of labeled glucose and unlabeled lactose to an individual and assessing labeled carbon dioxide in breath or blood. If the lactose is digested, the labeled $CO_2$ produced by the labeled glucose is diluted by the metabolism of the lactose.

9 Claims, 3 Drawing Sheets

REVERSE ISOTOPE DILUTION ASSAY AND LACTOSE INTOLERANCE ASSAY

PRIOR RELATED APPLICATIONS

This application claims priority to prior foreign application Japan No. 2001-583819, filed on Jan. 18, 2002, is a continuation and claims priority to prior International patent application No. PCT/US01/15143, filed May 10, 2001, which claims priority to U.S. provisional patent application Ser. No. 60/205,342, filed on May 18, 2000, all of which are incorporated herein by reference in their entirety.

FEDERALLY SPONSORED RESEARCH STATEMENT

Not applicable.

REFERENCE TO MICROFICHE APPENDIX

Not applicable.

FIELD OF THE INVENTION

The invention relates to a novel assay for monitoring for disease or metabolic dysfunction called a "reverse isotope dilution assay" or "RID" herein, wherein a pathway that produces a given metabolite is assayed by diluting the metabolite with the same metabolite produced by a second, constitutive pathway. More specifically, the invention relates to co-administering a "reverse tracer" molecule and an unlabeled substrate molecule to an individual. Both the reverse tracer molecule and the substrate molecule are metabolized to an equivalent end point, for example, $CO_2$. However, the "reverse tracer" molecule, by definition, is metabolized via a fast acting, constitutive pathway that differs from the pathway to be assayed. Thus, when the substrate molecule is added, and the pathway of interest is active, the reverse tracer metabolite will be diluted by the activity of the pathway of interest. In contrast, if the pathway is not active, the labeled metabolite will not be diluted. Thus, the activity of the pathway of interest can be determined from the dilution of the reverse tracer metabolite.

In one aspect, the invention relates to a method for monitoring "lactose maldigestion" or "lactose intolerance" in humans. Specifically, the method requires administering a tracer amount of labeled glucose and a physiological or pharmacological dose of unlabeled lactose to an individual and assessing labeled carbon dioxide in breath or blood.

BACKGROUND OF THE INVENTION

Carbon dioxide is an end product of cellular metabolism. It is expired in humans at a rate of 9 mmol/kg-hour (1) The rate of $^{13}CO_2$ production form $^{13}C$-labeled substrates has been demonstrated in cells, tissues, perfused organs and whole animals since the 1940s (2). Moreover, this approach has been used in biomedicine to measure liver function, malabsorption, bacterial infection, enzyme deficiency, pancreatic insufficiency and protein metabolism.

The principle of $^{13}CO_2$ breath tests is to administer a substrate labeled with $^{13}C$ either orally or intravenously. The substrate must possess a target bond that is attacked by a specific enzyme whose activity is to be measured. The enzymatic cleavage of the $^{13}C$ bond is the rate limiting step. Ultimately, the $^{13}C$ moiety is directly hydrolyzed or rapidly converted to $^{13}CO_2$.

Existing $CO_2$ tests generally require large amounts of labeled substrate. Tests based on radioactive labels are problematic because the patient consumes radioactive material. Disposal and handling costs also increase with radioactive labels. If non-radioactive labels are employed, the problems are not eliminated because labeled substrates are very expensive, thus increasing the costs of such tests significantly. What is needed in the art is a method that decreases the amount and cost of label required for a metabolic test, without sacrificing the needed sensitivity. The invention described herein, fulfills this need and, although exemplified with respect to a lactose intolerance assay, can be used wherever $CO_2$ breath tests are used. The invention can also be used for metabolites other than $CO_2$ and for samples other than breath samples.

Lactose maldigestion is the inability to digest significant amounts of lactose, the predominant sugar of milk. This inability results from a shortage of the enzyme lactase that is normally produced by the cells that line the small intestine. When there is not enough lactase to digest the amount of lactose consumed, the results may be very distressing and can result in dangerous dehydration among children. Common symptoms include nausea, cramps, bloating, gas, and diarrhea, which begin about 30 minutes to 2 hours after eating or drinking foods containing lactose. The severity of the symptoms varies depending on the amount of lactose each individual can tolerate.

The intestinal enzyme lactase ($\beta$-D-galactosidase) is responsible for metabolizing lactose. At birth, humans have abundant lactase activity in the small intestine but in most ethnic groups this activity decreases significantly during childhood between ages 3 to 5. Under conditions of lactase deficiency the lactose passes unmetabolized through the small intestine, drawing in copious amounts of water by osmosis. Next, the lactose passes into the large intestine and is fermented by colonic bacteria. Through these two processes, osmosis and fermentation, the typical symptoms associated with lactose maldigestion such as bloating, cramping, excessive gas and explosive diarrhea are derived.

Milk and other dairy products are a major source of nutrients in the American diet. The most important of these nutrients is calcium. Calcium is essential for the growth and repair of bones throughout life, but is a particular concern during the developmental years. In the middle and later years, a shortage of calcium may lead to thin, fragile bones that break easily; a condition known as osteoporosis. A concern, then, for both children and adults with lactose maldigestion, is getting enough calcium in a diet that contains little or no milk.

Studies have shown that nearly 50% of people who self-report milk intolerance are not maldigesters (1–3). Instead, they suffer from a functional bowel disorder such as irritable bowel syndrome (IBS), recurrent abdominal pain (RAP) in children or some other gastrointestinal complication. In these self-reported milk intolerants, it has been found that there is a significant, unnecessary reduction in milk consumption and insufficient dietary calcium intake (4).

Lactose maldigestion is relatively easy to treat. No treatment exists to improve the body's ability to produce lactase, but the symptoms can be controlled. Many foods are now available that are lactose-reduced or even lactose-free. Moreover, chewable tablets of lactase are available without prescription that, when taken just prior to a lactose-containing meal, can alleviate many symptoms.

However, all of these proposed therapies and remedies are only advisable in the person who is truly a lactose maldigesters (truly deficient in the enzyme lactase). For the person who suffers, for example, from irritable bowel syndrome (IBS) but is misdiagnosed as lactase-deficient, the addition of lactase in the form of tablets or the change to lactose-free dairy products will not alleviate symptoms. Moreover, those self-treaters who avoid dairy under the mistaken impression that they are maldigesters, put themselves at risk for poor bone growth and repair, osteoporosis and other conditions that results from the unnecessary removal of dairy products from their diet.

The diagnosis of lactose maldigestion has relied on the interview process coupled with removing milk (and milk products) from the diet, laboratory tests and jejunal biopsy. We briefly describe the state of each measure.

The interview process during which a patient is quizzed as to the history of their gastrointestinal symptoms and its relation to milk intake is easy to perform and inexpensive. It is also overly simplistic and quite imprecise. First, nearly 50% of people who self-report milk intolerance are normal digesters of lactose and secondly, 70% of the people with lactase-deficiency (although symptomatic) fail to correlate the broad gastrointestinal symptoms of this disease to the intake of lactose or "milk sugar" (7).

A number of laboratory tests are available for the assessment of lactose maldigestion. The most often cited tests are the hydrogen breath test, lactose tolerance test and the stool acidity test. The hydrogen breath test measures the amount of hydrogen in the breath. Normally, very little hydrogen is detectable in the breath. However, in the case of the lactose maldigesters, the lactose passes into the colon unmetabolized where bacteria ferment it and various gases, including hydrogen are produced. The hydrogen is absorbed from the intestines, carried through the blood stream to the lungs and exhaled. In this test, the patient drinks a lactose-loaded beverage, and the breath is analyzed at regular intervals over several hours. Raised levels of hydrogen in the breath indicates that the lactose is not being properly digested.

The interpretation of the hydrogen breath test results can be confounded by a number of factors. First, 5–20% of maldigesters do not produce hydrogen, resulting in a lowered sensitivity for the test (8). A comparable percentage of non-producers has been found in children (9). This is due to either not having the flora capable of producing hydrogen or utilization of the hydrogen to produce methane. Secondly, careful patient preparation, including no teeth brushing on the morning of the exam, no smoking, sleeping or strenuous activity during the exam is absolutely mandatory in order to produce a reliable test (10). Also, for one month prior to the test, there should be no mechanical bowel cleansing or antibiotic use since both influence the type and quantity of colonic bacteria (10). Finally, a low carbohydrate, low fiber dinner the night before the test is advised. Any deviations from these recommendations will compromise the test.

In the lactose tolerance test, a fasted individual (>10 hours without eating) is given a liquid that contains a large lactose load (typically 2g/kg to a maximum of 50 g which is equivalent to the lactose content of one liter of milk). Several blood samples are taken over a period of two hours to measure the subject's blood glucose level. This result is used as an indication of how well that patient digests lactose.

Again, there are several drawbacks to this test method. This test uses a supraphysiological dose of lactose, which makes its generalization to normal milk or dairy ingestion questionable. It requires a minimum of four (4) needle sticks over 2 hours to measure glucose concentration and strict patient compliance to a fasted state. Moreover, it suffers from decreased specificity (13% false positive rates have been reported) since a flattened response requires differentiation from defective glucose absorption resulting from small bowel disease (11). It has been suggested in the medical literature that due to both false negative and false positive results "that routine estimation of blood glucose after lactose load is not a useful measurement in children and adults and should be abandoned" (12).

In a recent study, it was shown that in 300 subjects tested using both the hydrogen breath test and the lactose tolerance test, in 40% of the cases, the two tests did not agree (13). The study suggests, however, that the hydrogen breath test is better able to identify individuals with lactose malabsorption and those most likely to have symptoms.

Due to the required lactose loads in these two diagnostic tests and the associated danger from dehydration resulting from lactose-induced diarrhea, they are generally not used in infants and very young children. Infants and young children may instead be given the stool acidity test. Undigested lactose, fermented by bacteria in the colon, creates lactic acid and other short-chain fatty acids that can be detected in a stool sample. This test is only effective in completely lactose-dominated diets (such as infant formula or breast milk) and since the incidence of lactose maldigestion in infants is very low, it is not often utilized.

Jejunal biopsy is an effective method for establishing a level of a patient's lactase activity. However, it is highly invasive and used only on rare occasion. Because lactose maldigestion is not generally considered a dangerous health condition, such an expensive, invasive and uncomfortable procedure is not a useful alternative.

Thus, what is needed in the art is a reliable, sensitive lactose intolerance test that is non-invasive, cost effective and accurate. The reverse isotope dilution test, exemplified herein with respect to lactose intolerance, meets these needs.

SUMMARY OF THE INVENTION

Abbreviations and Definitions

Reverse Tracer—a labeled substrate for a second, constitutive pathway; exemplified herein as 13C-glucose when used in a lactose intolerance RID Reverse Tracer metabolite—the labeled metabolite produced by the metabolism of the reverse tracer in the second, constitutive pathway.

RID—Reverse Isotope Dilution, the assay described herein wherein a first enzyme is assayed by the dilution of a labeled metabolite produced by both the first enzyme and a second constitutive enzyme Substrate—an unlabelled substrate molecule that is metabolized by the enzyme of interest to produce the same metabolite that is produced by the metabolism of the reverse tracer; exemplified herein by lactose in the lactose intolerance RID.

The invention is a reverse isotope dilution assay that can be generally described as follows: A first enzyme to be assayed is quantified by the diluting effects of a measurable metabolite produced by the first enzyme (or downstream of the first enzyme). The metabolite is the same metabolite produced by the action of a second enzyme (or enzyme pathway). A reverse tracer is co-administered with a substrate specific to the first enzyme. The reverse tracer molecule is a labeled substrate molecule that is specific to the second pathway and is quickly and constitutively metabolized by the second enzyme and/or pathway to produce the labeled metabolite. Thus, if the labeled metabolite is diluted, it means the first pathway is active. If it is not diluted, it means that the first enzyme is not active. A typical dilution curve for a labeled metabolite is illustrated in FIG. 1.

The present invention is exemplified with respect to a lactose intolerance assay, but can be generally applied to any disease whose course can be traced by tracing the exhalation of labeled bicarbonate. Such tests include the *Helicobacter pylori* breath test (based on labeled urea), the human liver glycogen metabolism breath test (using naturally $^{13}$C-enriched carbohydrate); the gastric emptying test (based on labeled octanoate or acetate); the chemotherapy intolerance breath test (based on labeled erythromycin); the bacterial overgrowth test (based on labeled xylose or sorbitol); the hepatic function breath test (based on labeled aminopyrine, methionine, or phenylalanine, for example); and the pancreatic sufficiency breath test (based on labeled mixed triglycerides or corn starch).

We have shown the combination of the $^{13}$C-glucose reverse tracer with lactose for use in a lactose intolerance assay RID which is based on measuring $CO_2$ in the breath. However, other combinations are possible. For example, $^{13}$C-acetate reverse tracer and fructose substrate may be combined in a fructose malabsorption RID $CO_2$ breath test. An erythromycin breath test may be converted to RID with the use of $^{13}$C-acetate and unlabeled erythromycin. The *Helicobacter pylori* $CO_2$ breath test could also be adapted to RID with the use of labeled $^{13}$C-glucose and unlabelled urea. The following table provides additional examples of RID tests.

TABLE 1

RID Substrate and Reverse Tracer Combinations

| Reverse Tracer | Substrate | Function/Disease |
| --- | --- | --- |
| $^{13}$C-Acetate/$^{13}$C-glucose/ $^{13}$C-bicarbonate | Amino acids (methionine, phenylalanine, lysine) | Liver Function |
| $^{13}$C-Acetate/$^{13}$C-glucose/ $^{13}$C-bicarbonate | Carbohydrates (xylose, sorbitol) | Small Intestine Bacterial Overgrowth |
| $^{13}$C-Acetate/$^{13}$C-glucose/ $^{13}$C-bicarbonate | Triglycerides (triolein, tripalmitate) | Pancreatic Function |
| $^{13}$C-Acetate/$^{13}$C-glucose/ $^{13}$C-bicarbonate | Starch | Pancreatic Function |
| $^{13}$C-Acetate/$^{13}$C-glucose/ $^{13}$C-bicarbonate | Galactose | Liver Function |
| $^{13}$C-Acetate/$^{13}$C-glucose/ $^{13}$C-bicarbonate | Urea | Helicobacter pylori Infection |
| $^{13}$C-Acetate/$^{13}$C-glucose/ $^{13}$C-bicarbonate | Leucine | Crohn's Disease |

The above table shows that either $^{13}$C-acetate, $^{13}$C-glucose, or $^{13}$C-bicarbonate would work as the reverse tracers. For some tests, one of these substrate might be preferred for cost or biochemical reasons. Other $^{13}$C reverse tracers would function in the invention, such as $^{13}$C-glycine, $^{13}$C-octanoate, $^{13}$C-palmitate, $^{13}$C-formate, $^{13}$C-propionate, and $^{13}$C-urea; however, their costs are much higher.

The reverse tracer is generally labeled with non-radioactive, stable isotopes in order to minimize radioactive waste hazards and patient exposure, but other isotopes may be employed. Generally, $^{13}$C isotopes are preferred, but $^{2}$D, $^{15}$N, $^{34}$S, and the like may also be used as appropriate for the metabolite to be measured. Oxygen-labeled substrates are another possibility, but the expense of $^{18}$O substrates may be so high as to be unfeasible.

The invention can also be broadened to include reverse isotopic detection of metabolites other than bicarbonate. For example, it can be employed for $^{15}$N-labeled substrates coupled with the detection of $N_2$ gas in breath, or $NH_3$ or urea in blood or urine. For example, the *Helicobacter pylori* breath test could also be adapted to RID with the use of labeled $^{15}$N-ammonia or $^{15}$N-ammonium salt and unlabelled urea coupled with the detection of labeled $NH_3$ in the urine. Similarly, the method could be employed with deuterated substrates coupled with the detection of $^{2}$H in the breath. Lactose intolerance, bacterial overgrowth and rapid transit of food through the small bowel can all be assayed by a hydrogen breath test.

Measurement of labeled metabolites, such as $CO_2$, in breath or blood may be made by instruments capable of detecting isotopes such as mass spectrometry, laser assisted spectrometry, infrared spectrometry or other spectrometry instruments. Further, the method includes isotopic measure of $CO_2$ by continuous monitoring (Katzman et al., U.S. Pat. No. 6,186,958).

The assay herein is exemplified as a breath test, but a blood, fecal, saliva, urine, or other body fluid specimen test could also be performed, provided the appropriate reverse tracer and substrate combinations are chosen.

The present invention also provides a method and kit for the assessment of lactose maldigestion or lactose intolerance in humans. The method is as described above, and the kit contains at least a labeled tracer and an unlabeled substrate. The kit may also contain a sample collection device, including a breath collection device, and instructions for use. Collection devices, such as breath, blood, and urine collection devices are well known in the art and are not described herein.

One of the major benefits of the RID technology is the reduced cost of the medical diagnostic test. For example, in the diagnosis of lactose maldigestion, one could administer $^{13}$C-lactose to directly measure lactase enzyme activity. However, $^{13}$C-lactose is a very expensive tracer to synthesize because it is a disaccharide. Using $^{13}$C-glucose and unlabeled lactose in a RID-based test, the per test cost is only a few dollars compared to greater than $100 for the usual $^{13}$C-lactose-based test.

One embodiment of the invention is a method of assaying enzyme activity in a subject. The method comprises administering to a subject an effective amount of a reverse tracer, wherein said reverse tracer is a labeled molecule that is constitutively metabolized by the subject to produce a labeled metabolite. The subject is co-administering an effective amount of an unlabeled substrate, wherein said substrate is specifically metabolized by an enzyme to be assayed and wherein said substrate is metabolized by said enzyme to produce an unlabeled metabolite that is the same as the metabolite from the prior step. A specimen is collected from the subject and the amount of labeled metabolite in the specimen measured to determine the activity of said enzyme in said subject. The method may also comprise comparing the amount of labeled metabolite with a standard, whereby said comparing yields a measure of enzyme activity, and whereby said standard is the mean amount of labelled metabolite produced by a control population of healthy subjects.

In another embodiment, the method is a method of assessing metabolic dysfunction in a subject using steps similar to those above. The reverse tracer, substrate and metabolic dysfunction can be as described throughout or as listed in Table 1. In one particular embodiment, the reverse tracer is labeled glucose, the substrate is lactose and the RID is for lactose intolerance. In another embodiment, the reverse tracer is labeled glucose, the substrate is fructose and the RID is for fructose malabsorbtion.

DETAILED DESCRIPTION OF THE INVENTION

Figure 1:
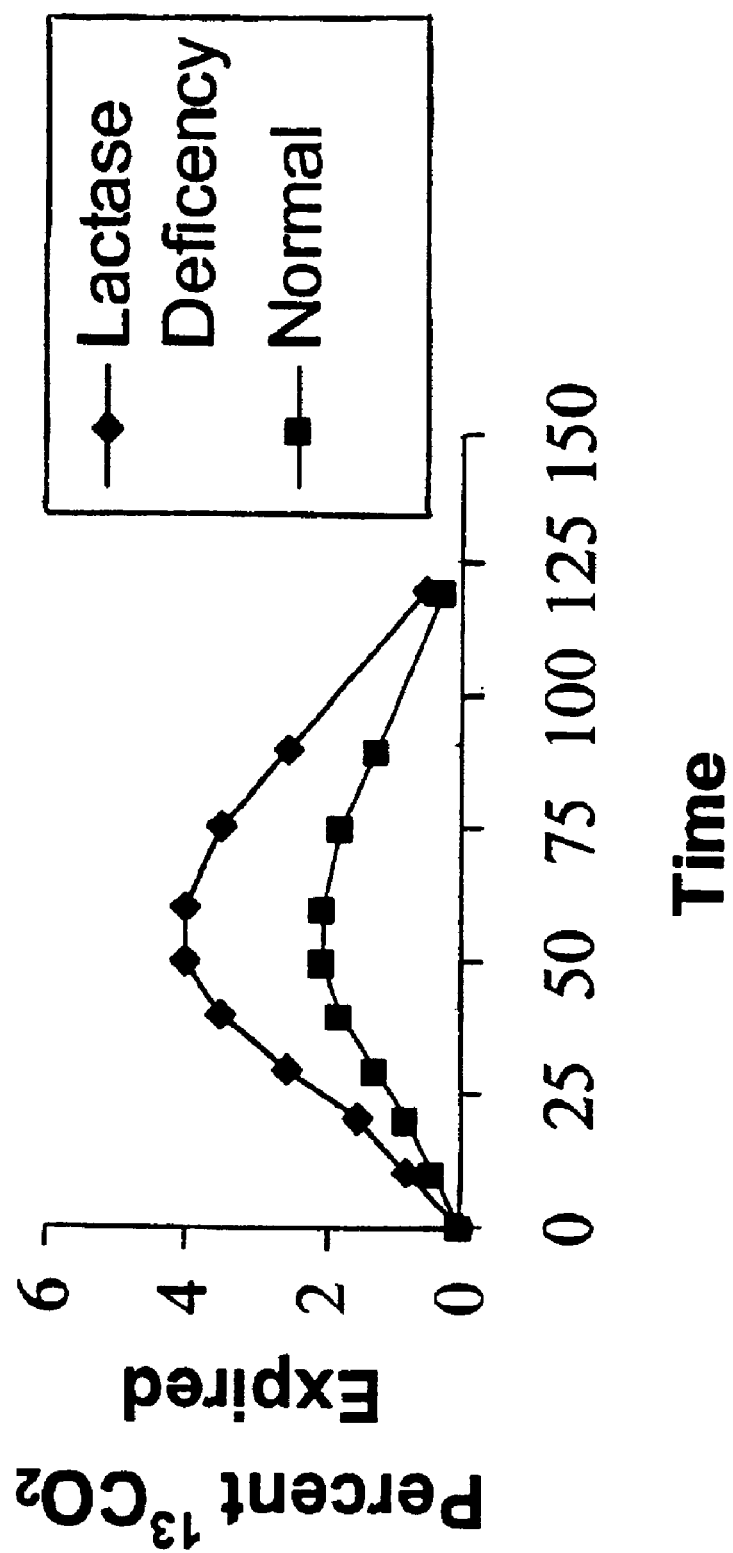
FIG. 1. is a $CO_2$ Dilution Curve (Lactose Intolerance)
Figure 2:
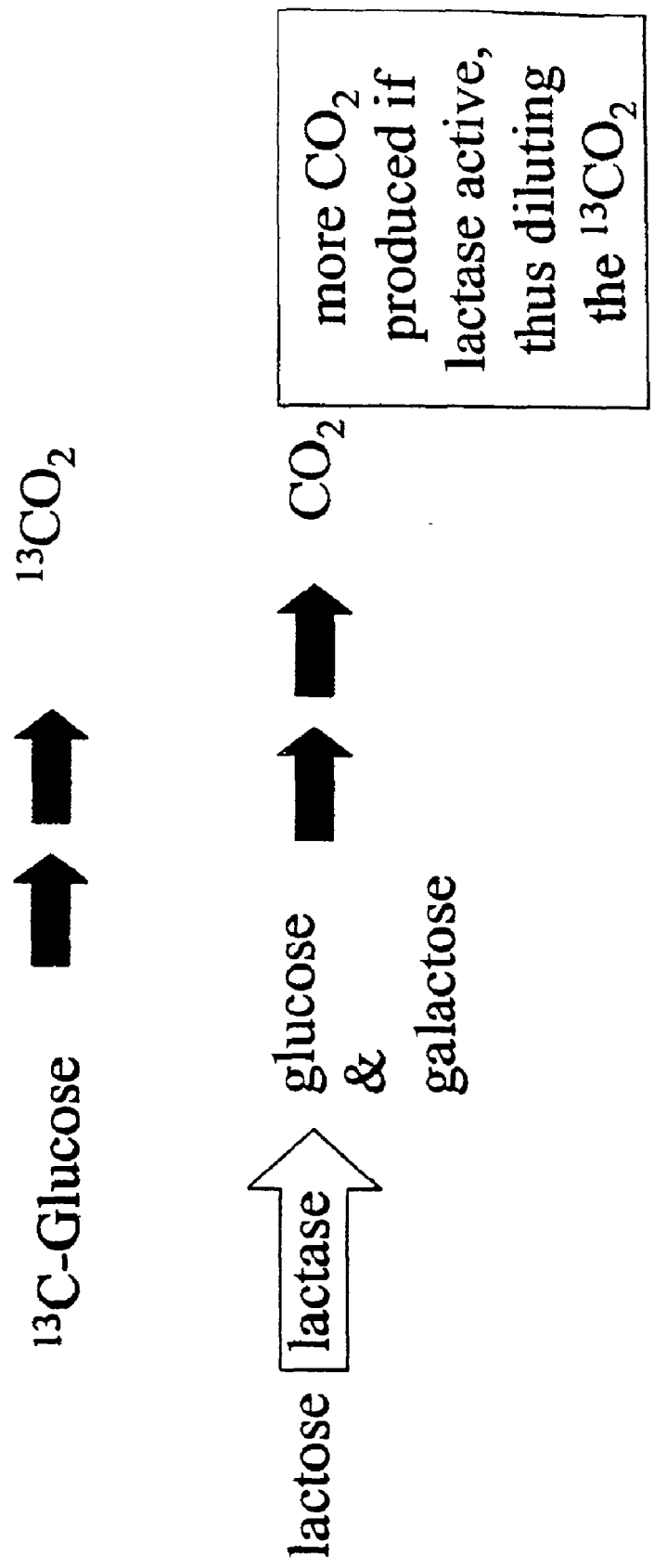
FIG. 2. is a Schematic Diagram of RID Concept

Provided herein is a method of assessing lactose maldigestion using reverse isotope dilution (RID) to measure enzyme rates directly by combining a labeled tracer and an unlabeled probe. The method uses a co-administration of 1-$^{13}$C-glucose (25 to 1000 milligrams) as a reverse tracer and unlabeled lactose (500 milligrams to 100 grams) as the test substrate. Unlabeled lactose is metabolized to glucose and galactose, which are subsequently converted rapidly to carbon dioxide. The administered 1-$^{13}$C-glucose is also rapidly metabolized to $^{13}CO_2$.

The amount of dilution of $^{13}CO_2$ in the breath or blood is indicative of the lactase enzyme activity. For the lactose maldigester, the 1-$^{13}$C-glucose tracer will appear undiluted in the breath as $^{13}CO_2$. That is, the results of the breath test, in the case the maldigester, will be the same whether lactose is administered or not. This is due to the fact that in the maldigester, lactose is minimally, if at all, converted to glucose and galactose. The normal digester on the other hand will generate unlabeled $CO_2$ from the lactose load (after processing through glucose and galactose) given with the test. This test demonstrates the degree of lactose maldigestion by measuring the amount of lactose digested via the amplitude of $^{13}CO_2$ arising from the 1-$^{13}$C-glucose reverse tracer in the breath.

The method further comprises comparing said amount of labeled carbon dioxide with a standard, whereby said comparing yields a measure of lactose maldigestion. The standard comprises the mean isotopic value of $CO_2$ in a control population without lactose maldigestion or lactose intolerance.

The following examples serve to illustrate specific embodiments of the invention, but should not be considered as a limitation on the scope of the invention.

EXAMPLE 1

Administration of the Test

All breath tests are performed after a minimum of 8 hours of fasting. Prior to the detection substrate administration, a baseline breath sample is collected using an alveolar gas collection system (QUINTRON GASAMPLER COLLECTION BAG™, QUINTRON INSTRUMENT COMPANY™, Milwaukee, Wis.). Subjects are administered a 10% aqueous lactose solution containing 25 grams of orange-flavored lactose (QUINTRON INSTRUMENT COMPANY™) in 250 ml tap water. In addition to the lactose, subjects consume 100 milligrams of 1-$^{13}$C-glucose (CAMBRIDGE ISOTOPE LABORATORIES™, Andover, Mass.) which is added to the aqueous lactose solution. End-alveolar breath samples are at evaluated for $^{13}$C enrichment in carbon dioxide at 0, 60 and 90 minutes.

EXAMPLE 2

Bicarbonate Measurement

The amount of $^{13}CO_2$ in breath storage tubes are measured with a EUROPA SCIENTIFIC™ 20/20 gas isotope ratio mass spectrometer (EUROPA SCIENTIFIC™, Cincinnati, Ohio). The ratio of $^{13}CO_2$ to $^{12}CO_2$ (mass 45 to 44) is measured in the sample and compared to a reference gas (5% $CO_2$, balance 75% $N_2$, 20% $O_2$). The reference gas is calibrated with international standards. The units of measurement are atom % $^{13}$C and defined by:

$$\text{Atom \% }^{13}C = {}^{13}CO_2/({}^{13}CO_2 + {}^{12}CO_2) * 100\%$$

Standards of carbon dioxide gas at 3 different levels of atom % $^{13}$C are run before and after each daily run to check instrument performance. The analytical precision of the instrument is 0.0001 atom % $^{13}$C.

The atom % $^{13}$C value of each breath sample is used to calculate the percent of the dose recovered in the breath during each time period. The area under the curve (AUC) for each time period, is calculated by the linear trapezoid method, using the atom % $^{13}$C for the two points during time period. The percent of the dose metabolized within each time period is calculated as:

Total $^{13}$C Excreted (mmol)=% $^{13}$C (AUC)×$CO_2$ production mmol/min×Time (min) where $CO_2$ production is estimated by 5 mmol/min/m²×body surface area (m²) % Dose Metabolized= Total $^{13}$C Excreted (mmol)/Dose (mmol)×100%.

EXAMPLE 3

Test Validity

Initial investigations established the validity of the test. One hundred twenty (120) subjects (51 males and 69 females) of ages greater than 18 years were evaluated for lactose maldigestion. Each subject was tested on two occasions following an overnight fast. The subject underwent a physical exam and was interviewed concerning their experience with dairy consumption. On Day 1, a 100 mg dose of D-glucose (1-$^{13}$C, 99%), (CAMBRIDGE ISOTOPE LABORATORIES™, Andover, Mass.) was diluted to with 25 ml with tap water. A 50 g dose of Lactose (QUINTRON, INC.™, Milwaukee Wis.) was simultaneously administered. Breath samples were collected for $^{13}CO_2/^{12}CO_2$ ratio measurement were collected at 5, 15, 30, 45, 60, 75, 90, 105 and 120 minutes from dosing. The samples were analyzed on A FINNIGAN BREATHMAT PLUS™ gas isotope ratio analyzer for the $^{13}C/^{12}C$ ratio of the exhaled $CO_2$. All of the breath test results were then converted to % dose metabolized per unit time.

At the same time, the hydrogen breath test (QUINTRON, INC.™, Milwaukee Wis.) and the Lactose Tolerance Test (blood glucose levels) were administered according to standard protocols. Further, urine was collected for the determination of galactose levels in the urine as another measure of lactose digestion. The next day (Day 2), the experiment was repeated but with load of lactose changing from 50 g to 25 g.

A major limitation to the analysis of the subsequent data was the absence of a "gold standard" for the diagnosis of lactose malabsorption. Even the most reliable test, the hydrogen breath test, reports accuracy at no better than 85%. Therefore, a new test, even if perfectly accurate, can not have an accuracy score above that of the gold standard (85%). For our study, in an attempt to address this limitation, a diagnosis of lactase status was determined by combining all of the reference methods and drawing a unifying diagnosis from the collection of results based on majority diagnostic opinion (2 of 3 tests). The Lactose Maldigestion Breath Test (LMBT) and each reference method (hydrogen breath test, blood glucose test and urinary galactose) were individually evaluated versus the unifying diagnosis. The following performance characteristics are shown in table 2. Note, the 25 gram hydrogen breath test was done on only 59 subjects while the other tests were performed on 120 subjects.

TABLE 2

Lactose Intolerance Validation

| Test | Sensitivity | Specificity | PPV | NPV | Accuracy |
|---|---|---|---|---|---|
| LMBT | 87% | 79% | 82% | 85% | 83% |
| Hydrogen Breath Test 50 grams | 87% | 80% | 83% | 85% | 84% |
| Hydrogen Breath Test 25 grams | 75% | 100% | 100% | 82% | 88% |
| Blood Glucose Test | 78% | 84% | 84% | 77% | 81% |
| Urinary Galactose Test | 55% | 82% | 77% | 62% | 66% |

PPV = Positive Predictive Value
NPV = Negative Predictive Value

Although samples were collected every 15 minutes, we were able to differentiate lactose digesters from maldigesters using only the baseline, 60 and 90-minute samples without any loss of accuracy. If the test was positive at 60 minutes, in theory, the test could be stopped. The fact that the test can be completed within 90 minutes prevents potential problems associated with glucose being metabolized by the colonic flora. Generally intestinal transit or oro-cecal time is normally at least 75 minutes or more.

Based on these studies with adults, the following cutoff values can be used to define lactose malabsorption:
At 60 minutes, greater than 1.50% $^{13}$C glucose metabolized
At 90 minutes, greater than 4.50% $^{13}$C glucose metabolized
At 120 minutes, greater than 7.50% $^{13}$C glucose metabolized

EXAMPLE 4

Fructose Malabsorbance RID

Although not yet fully validated, a RID has been exemplified for a fructose malabsorbance breath test. In the test, the patient is co-administered labeled acetate and unlabelled fructose. If the patient is unable to absorb and utilize the fructose, the $^{13}CO_2$ levels remain high whereas in the normal patient the $^{13}CO_2$ levels are diluted by concomitant absorption and metabolism of the unlabelled fructose.

Figure 3:
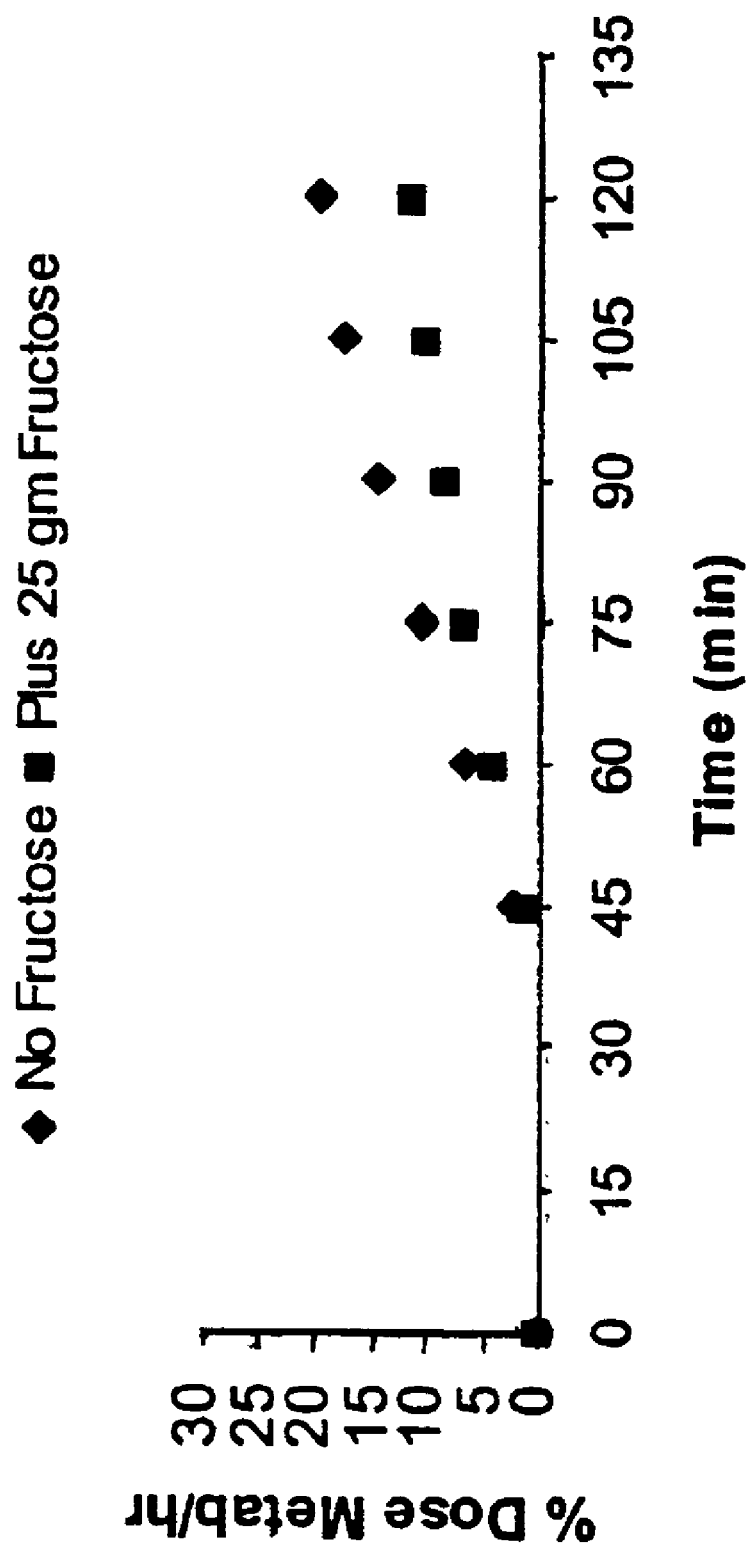
FIG. 3. is a $CO_2$ Dilution Curve (Fructose Malabsorption)

FIG. 3 shows the results of one subject administered 100 mg sodium 1-$^{13}$C-acetate with and without 25 grams fructose. The graph shows the plot of the percent acetate metabolized to carbon dioxide per unit time. In this subject, since fructose is absorbed and itself converted to carbon dioxide, it dilutes the amount of $^{13}$C appearing in breath carbon dioxide. For a subject who does not absorb fructose, the two breath $^{13}$C excretion curves would be identical.

Each reference is listed herein for convenience, and is incorporated by reference in its entirety.

1. Suarez, F. L., et al., (1995) N. Engl. J. Med. 333:1–4.
2. Saltzman, J. R., et al., (1999) Am. J. Clin. Nutr. 69:140–6.
3. Peuhkuri, K., et al., (2000) Am. J. Clin. Nutr. 71:600–1.
4. Stallings, V. A., (1997) Am J. Ther. 4: 259–273.
5. Montes, R. G. and Perman, J. A., (1991) Postgrad. Med. 89: 175–184.
6. Srinivasan, R. and Minocha, A., (1998) Postgrad. Med. 104: 109–123.
7. Carrocio, A., et al., (1998) J. Am. Coll. Nutr. 17:631–36.
8. Davidson, G. P., et al., (1984) J. Pediatr. 105:587–90.
9. Douwes, A. C., et al., (1985) Arch. Dis. Child. 60: 333–7.
10. Arola, H. (1994) Scand. J. Gastroenterol. 29 (Suppl 202):26–35.
11. Douwes, A. C., et al., (1978) Arch. Dis. Child. 53: 939–942.
12. Harrison, M. and Walker-Smith, J. A., (1977) Gut 18: 48–52.
13. Hermans, M. M., et al., (1997) Am. J. Gastroenterol. 92:981–4.
14. U.S. Pat. No. 6,186,958

What is claimed is:

1. A method of assaying enzyme activity in a subject, said method comprising:
    a) administering to a subject an effective amount of a reverse tracer wherein said reverse tracer is a carbon labeled molecule that is constitutively metabolized by the subject to produce a labeled metabolite wherein said carbon labeled molecule is selected from the group consisting of acetate, glucose, bicarbonate, glycine, octanoate, palmitate, formate, propionate, and urea;
    b) administering to said subject an effective amount of an unlabeled substrate, wherein said substrate is specifically metabolized by an enzyme to be assayed and wherein said substrate is metabolized by said enzyme to produce and unlabeled metabolite that is the same as the metabolite from step a);
    c) collecting a specimen from said subject; and
    d) measuring the amount of labeled metabolite in said specimen to determine the activity of said enzyme in said subject wherein the dilution of labeled metabolite indicates enzyme activity.

2. The method according to claim 1, wherein said carbon-labeled molecule is selected from the group consisting of a $^{13}$C labeled molecule, a $^{14}$C labeled molecules, and mixtures thereof.

3. The method according to claim 1, wherein said carbon-labeled molecule is labeled at the 1-position.

4. The method according to claim 1, wherein said carbon-labeled compound comprises a plurality of labeled carbons.

5. The method according to claim 1, wherein said metabolite is carbon dioxide.

6. The method according to claim 5 wherein said labeled metabolite is $^{13}$C carbon dioxide.

7. The method according to claim 1, further comprising comparing said amount of labeled metabolite with a standard, whereby said comparing yields a measure of enzyme activity, and whereby said standard is the mean amount of labelled metabolite produced by a control population of healthy subjects.

8. A method according to claim 1 wherein said enzyme is lactase, said reverse tracer is selected from the group consisting of $^{13}$C labeled glucose, $^{13}$C labeled glucose, and mixtures thereof said unlabeled substrate is lactose; and said labeled metabolite is selected from the group consisting of $^{13}$C labeled $CO_2$, $^{14}$C labeled $CO_2$, and mixtures thereof.

9. A method according to claim 1 wherein:
    a) said enzyme is lactase, said reverse tracer is $^{13}$C labeled glucose, said unlabeled substrate is lactose, and said labeled metabolite is $^{13}CO_2$;
    b) said enzyme is lactase, said reverse tracer is $^{14}$C labeled glucose, said unlabeled substrate is lactose, and said labeled metabolite is $^{14}CO_2$;
    c) said enzyme is lactase, said reverse tracer is $^{13}$C labeled acetate, said unlabeled substrate is lactose, and said labeled metabolite is $^{13}CO_2$;
    d) said enzyme is lactase, said reverse tracer is $^{14}$C labeled acetate, said unlabeled substrate is lactose, and said labeled metabolite is $^{14}CO_2$;

e) said enzyme is lactase, said reverse tracer is $^{13}C$ labeled bicarbonate, said unlabeled substrate is lactose, and said labeled metabolite is $^{13}CO_2$;

f) said enzyme is lactase, said reverse tracer is $^{14}C$ labeled bicarbonate, said unlabeled substrate is lactose, and said labeled metabolite is $^{14}CO_2$;

g) said enzyme is a fructose transporter protein, said reverse tracer is $^{13}C$ labeled glucose, said unlabeled substrate is fructose, and said labeled metabolite is $^{13}CO_2$;

h) said enzyme is a fructose transporter protein, said reverse tracer is $^{14}C$ labeled glucose, said unlabeled substrate is fructose, and said labeled metabolite is $^{14}CO_2$;

i) said enzyme is a fructose transporter protein, said reverse tracer is $^{13}C$ labeled acetate, said unlabeled substrate is fructose, and said labeled metabolite is $^{13}CO_2$;

j) said enzyme is a fructose transporter protein, said reverse tracer is $^{14}C$ labeled acetate, said unlabeled substrate is fructose, and said labeled metabolite is $^{14}CO_2$;

k) said enzyme is a fructose transporter protein, said reverse tracer is $^{13}C$ labeled bicarbonate, said unlabeled substrate is fructose, and said labeled metabolite is $^{13}CO_2$; and l) said enzyme is a fructose transporter protein, said reverse tracer is $^{14}C$ labeled bicarbonate, said unlabeled substrate is fructose, and said labeled metabolite is $^{14}CO_2$.

\* \* \* \* \*

UNITED STATES PATENT AND TRADEMARK OFFICE
CERTIFICATE OF CORRECTION

PATENT NO. : 6,902,719 B2  Page 1 of 1
DATED : June 7, 2005
INVENTOR(S) : David A. Wagner It is certified that error appears in the above-identified patent and that said Letters Patent is hereby corrected as shown below:

<u>Column 10,</u>
Line 24, replace "and" with -- an --.
Line 34, replace "$^{14}$C labeled molecules" with -- $^{14}$C labeled molecule --.
Line 47, replace "labelled" with -- labeled --.
Line 50, replace the second occurrence of "$^{13}$C labeled glucose" with -- $^{14}$C labeled glucose --.
Line 51, insert a -- ; -- after "thereof".

Signed and Sealed this

Eleventh Day of April, 2006

JON W. DUDAS
*Director of the United States Patent and Trademark Office*